United States Patent [19]
Johnson, Jr. et al.

[11] Patent Number: 4,511,358
[45] Date of Patent: Apr. 16, 1985

[54] URINE BAG CARRIER WITH A STRETCHABLE FRONT PANEL

[76] Inventors: Clifford B. Johnson, Jr.; Barbara Johnson, both of 200 NE. Fifth Ave.; Alex Amadio; Williane Amadio, both of 1120 S. Parrott Ave., all of Okeechobee, Fla. 33472

[21] Appl. No.: 430,843

[22] Filed: Sep. 30, 1982

[51] Int. Cl.³ .............................................. A61M 1/00
[52] U.S. Cl. .................................. 604/327; 224/191; 604/345; 604/353
[58] Field of Search ............... 224/226, 258, 148, 191; 604/317, 327, 329, 331, 343, 345, 353; 383/112, 118; 215/11 E; 128/769

[56] References Cited

U.S. PATENT DOCUMENTS

| 1,416,238 | 5/1922 | Sciler | 224/226 |
| 2,133,130 | 10/1938 | Buchstein | 128/349 |
| 2,756,751 | 7/1956 | Smith | 604/353 |
| 2,945,614 | 7/1960 | Wittmann, Sr. | 224/148 |
| 3,306,296 | 2/1967 | Moss | 128/295 |
| 3,601,125 | 8/1971 | Moss | 128/295 |
| 3,897,785 | 8/1975 | Barto, Jr. | 604/327 |
| 3,999,550 | 12/1976 | Martin | 604/353 |
| 4,055,201 | 10/1977 | Fowler | 383/118 |
| 4,073,295 | 2/1978 | Laufbahn | 128/295 |
| 4,122,851 | 10/1978 | Grossner | 604/353 |
| 4,173,979 | 11/1979 | Odis | 604/327 |
| 4,390,116 | 6/1983 | Fehr | 224/258 |
| 4,457,314 | 7/1984 | Knowles | 604/327 |

FOREIGN PATENT DOCUMENTS

| 657004 | 2/1963 | Canada | 604/349 |
| 2084879 | 4/1982 | United Kingdom | 604/317 |

Primary Examiner—C. Fred Rosenbaum
Assistant Examiner—J. L. Kruter
Attorney, Agent, or Firm—Sherman & Shalloway

[57] ABSTRACT

This invention provides a urine leg drainage bag supporter comprising a waist encircling belt; a pouch for holding a urine bag, the pouch being formed of front and back panels connected at the vertical edges to define an opening in the top and bottom portions of the pouch, the front panel being formed of a stretchable material to firmly hold the bag within the pouch; a plurality of vertical straps connecting the pouch to the belt; and a plurality of horizontal straps extending from the pouch for encircling the leg of the wearer.

9 Claims, 7 Drawing Figures

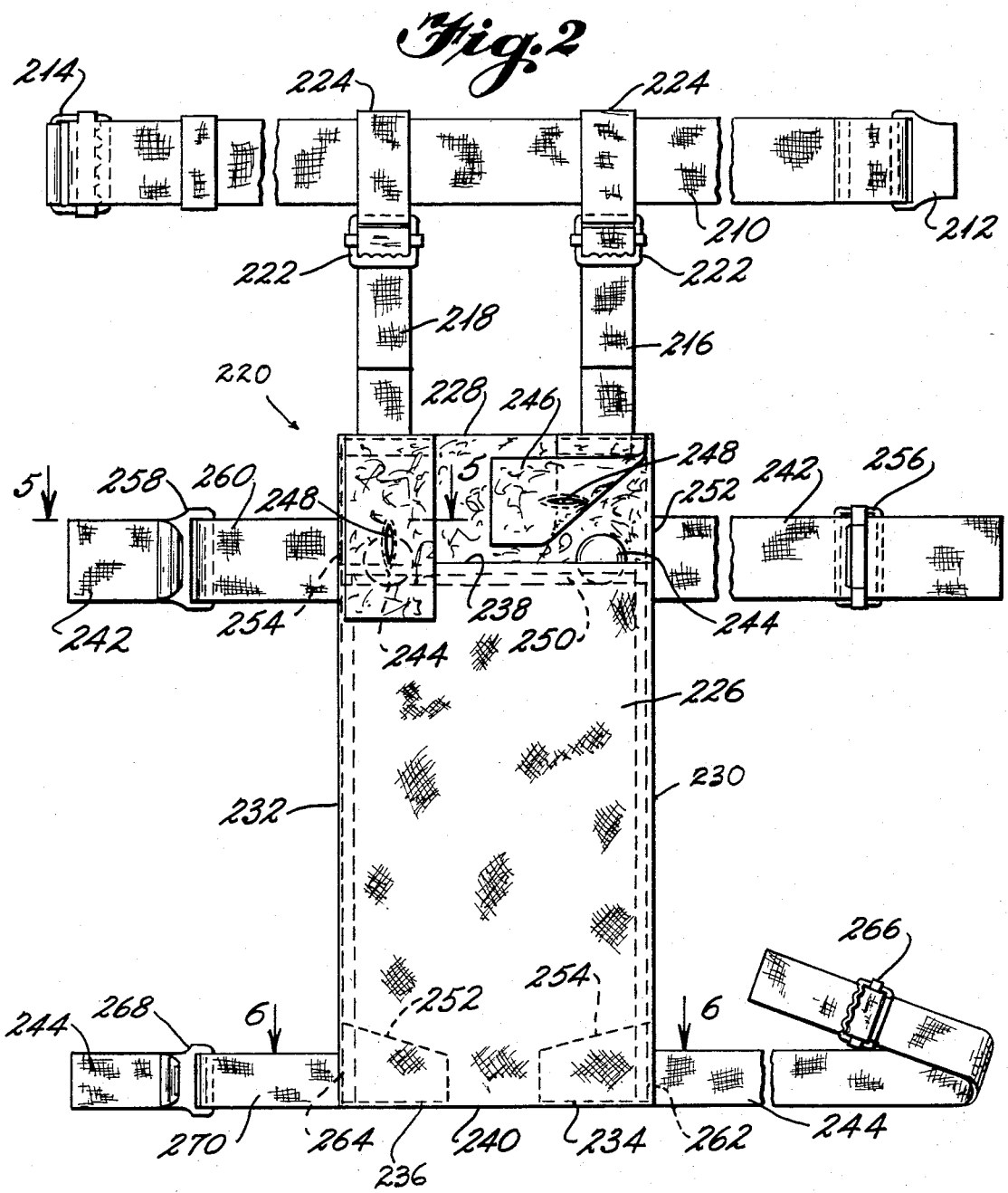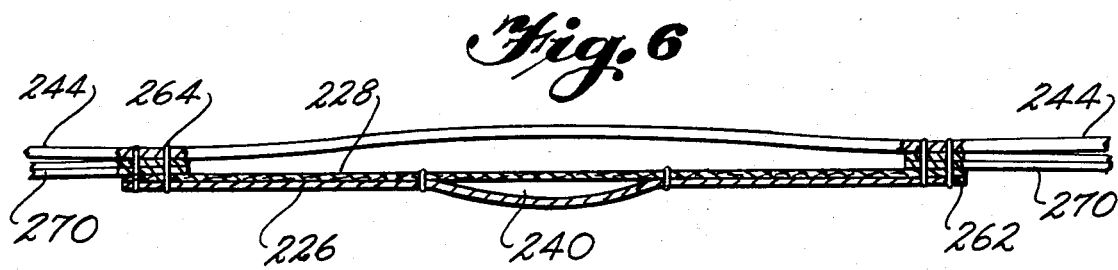

U.S. Patent   Apr. 16, 1985   Sheet 3 of 3   4,511,358
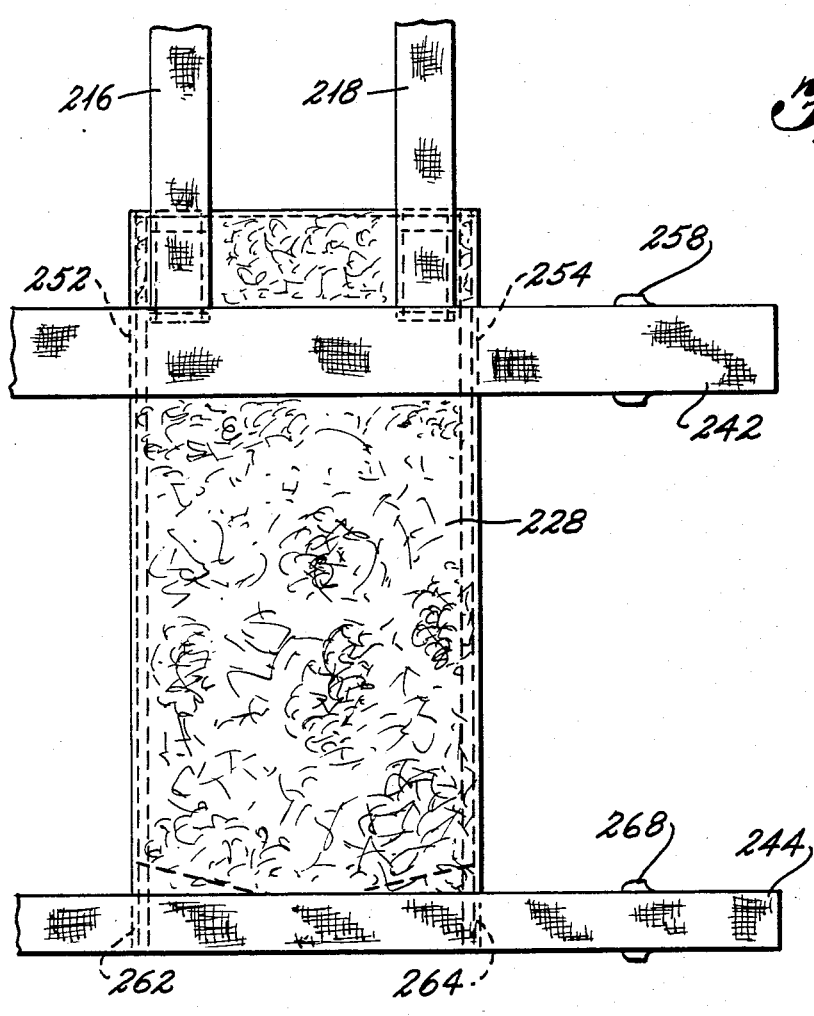
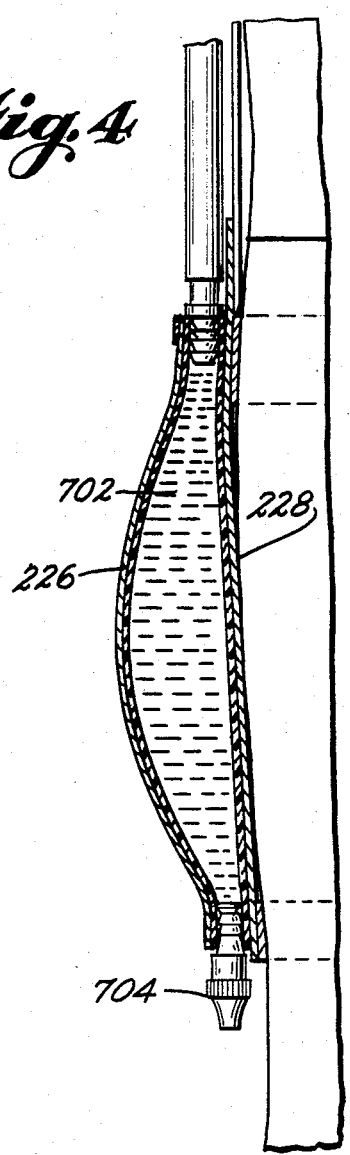
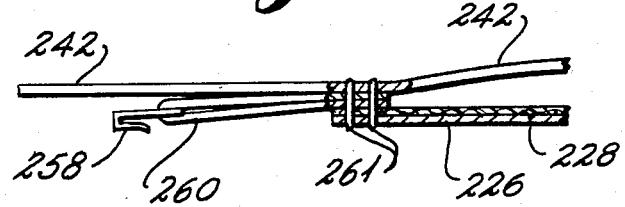

URINE BAG CARRIER WITH A STRETCHABLE FRONT PANEL

BACKGROUND OF THE INVENTION

1. Field of the Invention

This invention relates to urine leg drainage bag supporters. More specifically, this invention is directed to belt-supported urine bag supporters.

2. Description of the Prior Art

Those individuals who are afflicted with certain urological diseases so that the urinary tract is blocked or loses its ability to retain the natural discharge of urine from the body are usually provided with a device for collecting and storing the urine. A common method comprises fitting the patient with an indwelling urinary bladder drainage catheter which is connected by means of a long extension tube to a vinyl urine collecting bag. The collecting bag is usually carried by hand when the patient is in a standing position. When the patient is in a sitting position or when the patient wishes to free his/her hands, the bag is usually hung or otherwise attached to a chair or table edge. As is apparent, this type of urine collection device severely limits the type of clothing the patient can wear in conjunction therewith. More importantly, the appearance which such a device presents in public causes embarrassment, anxiety and emotional distress in the patient.

In another type of conventional urine collection device, a much smaller vinyl collection bag is used. The bag is rectangular in shape and is provided with an inlet in the top portion thereof and a drain valve in the bottom. The open end of the indwelling urinary bladder catheter is connected to the inlet of the bag which has disposed therein a flutter valve for the prevention of back flow of the urine into the body. The urine enters the bag through the top inlet and is drained from the bag through the bottom twist valve which is usually formed of a rigid plastic material. The bag usually can hold about 300 ml of urine. The bag is normally held to the thigh of the patient by means of two one-inch elastic rubber straps. Although this type of collection device can be hidden from view underneath of the patient's clothing, the device suffers from some severe disadvantages. First; the rubber straps have the tendency to curl up and roll down the patient's leg. This problem is intensified as the bag becomes more filled with urine. Pulling or tugging of the catheter causes pain, irritation and even bleeding in the bladder. Second, the rubber straps if worn for an extended period of time cause primary skin irritation due to the pressure, heat, friction and lack of air circulation between the straps and the patient's skin. Third, since the straps are elastic, they are incapable of holding up the weight of the bag as it is filled with urine, even if the straps lay flat against the patient's thigh and are positioned high up on the thigh. Also as a consequence of the elastic nature of the straps, the position of and tension on the straps must be constantly adjusted as the bag fills with urine. On the other hand, if the straps are stretched too tightly around the leg, this may cause leg pain as well as restrict blood circulation in the leg. Fourth, if the bag becomes too full and the straps fail, the bag may fall, thus causing a spill out of the urine or inflicting severe pain in the patient as the indwelling catheter is subjected to a sharp outward pull.

Furthermore, the positioning of the urine bag flat against the patient's thigh has numerous disadvantages. The large surface area of the bag in constant contact with the skin can cause irritation, chafing, itching and even infection. Small amounts of urine leaked from the catheter/bag inlet connection can seriously complicate the problem. As the bag fills, the urine is collected at the bottom portion thereof, causing the bottom portion to bulge and forcing the lower edge of the bag to curl inwardly, i.e. toward the patient, which forces the rigid drain valve to press against the patient's skin. This pressure increases as the bag becomes more filled. It has also been found that when the bag, which usually has a capacity of about 300 ml, is filled to about 75 ml, the weight becomes too great for the rubber straps to hold the bag firmly which leads to shifting or sliding of the bag and pain in the patient. This leads to inefficient use of the bag volume. Moreover, continuous shifting and moving of the bag are accompanied by constant pulling or tugging on the catheter attached thereto. Such constant movement of the catheter can produce irritation along the inner surface of the urinary bladder which, in turn, may cause chronic bleeding. This bleeding may directly contribute to infection of the bladder, prostate, urethra and cystotomy stoma or opening. Because of the filling of the bag and the increase in weight, the range of motion of the leg trunk and body of the patient is progressively restricted. Even when the patient is in a horizontal position, when the bag becomes half full, it begins to shift and pull therewith the attached catheter which leads to bladder spasms, pain, loss of sleep, etc. Furthermore, when the bag is filled to capacity overnight, it will have shifted to rest on the mattress. As a result, the bag is without any effective support when the patient struggles to rise and empty the bag. Each motion causes movement in the bag which is accompanied by sharp pain as the bag pulls on the catheter which moves within the bladder cavity.

From the above description, it is clear that the conventional method of securing a urine bag to the patient's thigh by means of elastic straps is highly painful to the patient and needs much improvement. The present invention is made to correct all of the above defects found in connection with the conventional method.

SUMMARY OF THE INVENTION

This invention provides a urine leg drainage bag supporter comprising a waist encircling belt, a pouch in which the urine bag is inserted, and a plurality of horizontal straps extending from the top and bottom portions of the pouch, the straps being for encircling the leg of the wearer, the pouch being connected to the belt by means of a plurality of vertical straps, all straps having adjustable lengths. The pouch is formed of a front and a back panel, both panels being sewn together on their side edges so as to define an opening in the top and bottom of the pouch, respectively. The front panel of the pouch is formed of a stretchable material in order to prevent the urine bag from taking the shape of a tear drop, i.e. bulging out at the bottom, as urine flows into the bag. By using a stretchable front panel and special stitching in attaching the horizontal straps to the top and bottom parts of the pouch, the bag is held firmly within the pouch and the curling in of the bottom drain valve and bulging in the bottom portion of the bag as it is filled are prevented. This results in a urine leg drainage bag supporter which can be comfortably worn by the patient for extended periods of time. The pain and suffering associated with conventional urine bag carriers are substantially eliminated.

BRIEF DESCRIPTION OF THE DRAWINGS

FIG. 2 illustrates the front view of the present urine leg drainage bag supporter.

FIG. 3 illustrates the back view of the present urine leg drainage bag supporter.

FIG. 4 shows the cross-sectional view along line 4—4 in FIG. 1.

FIG. 5 shows the cross-sectional view along line 5—5 in FIG. 2.

FIG. 6 illustrates the cross-sectional view along line 6—6 in FIG. 2.

DESCRIPTION OF THE PREFERRED EMBODIMENT

According to the present invention, there is provided a urine leg drainage bag supporter which supports, immobilizes and contains the urine bag irrespective of the position of the wearer, the volume of urine contained in the bag, the physical size of the wearer or whether the catheter emerges from the bladder through the urethra (the natural opening) or a cystotomy opening. The present invention allows the wearer freedom of movement to enable him to participate in any type of activity without fear of an accidental urine leakage due to a sudden disconnection resulting from shifting of the bag. Furthermore, the present carrier is so designed that it can be worn, adjusted or removed easily.

Figure 1:
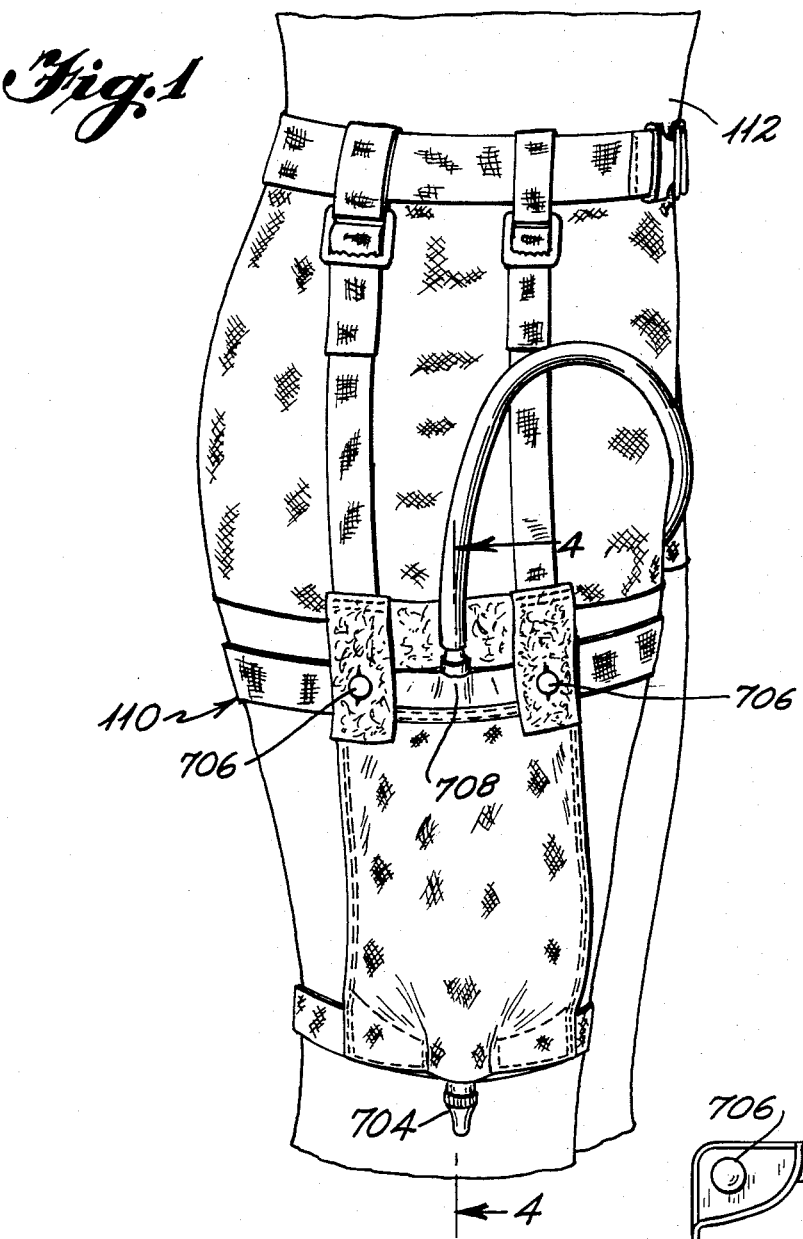
FIG. 1 shows the present urine leg drainage bag supporter as worn by a patient.

With reference to the drawings, FIG. 1 shows the present urine bag carrier 110 as worn by a patient 112. As shown in further detail in FIG. 2, the present carrier comprises a belt 210 for encircling the waist of the wearer. The ends of belt 210 are provided with a fastener means. As shown in FIG. 2, one of belt 210 is fixed to the hook portion 212 of a slip buckle whereas the other end is fed through the loop portion 214 of the buckle. Although a slip buckle is shown in FIG. 2, any other fastener means which can be easily and conveniently fastened and unfastened can also be used. The belt may be formed of any suitable material. A 1½ inch wide all cotton orthopedic belting has been found to be the most preferred material for belt 210 since it is strong enough to support the filled bag, and can be laundered easily, and is non allergenic. A stainless steel slip buckle is preferred because it offers convenient fastening and unfastening, does not cause skin irritation, is most reliable and is lightweight.

Connected to belt 210 are two vertical straps 216 and 218. One end of these vertical straps extends down the back panel of pouch 220 and is stitched to the top portion of pouch 220. The other and free end is fed through the loop portion of a slip buckle 222. Also fed through the loop portion of buckle 222 is a separate movable cotton orthopedic belt loop 224 which encircles belt 210 so that vertical straps 216 and 218 are suspended from belt 210. The above described method of suspending straps 216 and 218 from belt 210 is given as the preferred method.

Vertical straps 216 and 218 serve to suspend pouch 220 and belt 210 and support the weight of the pouch and the urine bag contained therein. By using the slip buckles, the length of the vertical straps can be varied to suit patients of different body lengths. It has been found that 1 inch wide orthopedic woven belting is the preferred material for use as vertical straps 216 and 218. Such material provides the most comfort and least amount of distortion under varying conditions of filled bag volume and body position of the patient.

Figure 7:
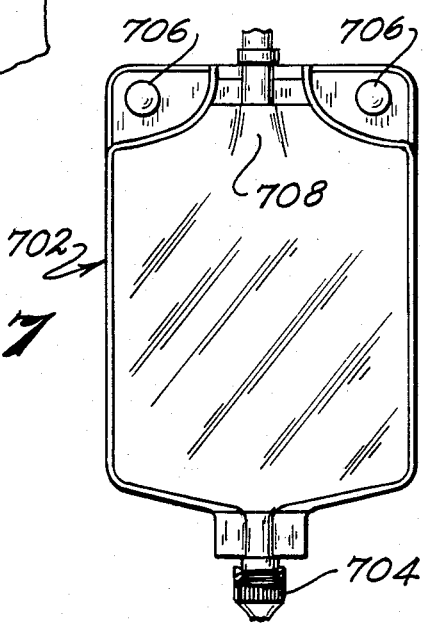
FIG. 7 shows a conventional urine bag.

Pouch 220 has the general configuration of a rectangle and is of sufficient size to hold a conventional vinyl urine bag, as shown in FIG. 7, which has the same shape. The pouch comprises front panel 226 and back panel 228. The panels are sewn together along the vertical side edges by side stitchings 230 and 232 and partially along the bottom edge by bottom stitches 234 and 236. As a result, top opening 238 and bottom opening 240 which is disposed about the center of the bottom edge are formed in pouch 220. Top opening 238 which extends across the entire width of the pouch is adapted for easy insertion of the urine bag into the pouch. As to bottom opening 240, it is for the projection therethrough of drain valve 704 (FIG. 7) provided at the bottom of conventional urine bag 701.

Attached to back panel 228 are a plurality of straps. As has been described above, vertical straps 216 and 218 are sewn or otherwise attached to the top portion of a back panel 228. Below the vertical straps, upper horizontal strap 242 is attached to the back panel. Near the bottom of the back panel, lower horizontal strap 244 is sewn to the back panel. The manner in which the upper and lower straps are attached to the back panel is described in detail hereinbelow.

To secure conventional urine bags having thereon button-holes to the back panel, two buttons 244 are provided near the top of, usually about two inches from the top edge of the back panel. For those urine bags which are formed with buttons therein (706 in FIG. 7), two tabs 246 each having a button-hole 248 are provided to suspend and stabilize the vinyl urine bag as it hangs within the pouch. One end of tab 246 is sewn to the top edge of back panel 228, as shown in the drawing.

Since back panel 228 forms the surface which comes in constant contact with the patient's skin, the material used to form the back panel must be carefully selected in order not to irritate the skin. To this end, it has been found that terry cloth is the preferred material because of its softness, absorbancy and durability.

Front panel 226 is formed of a stretchable material, suitable examples being polyester knit fabrics. Elastic band 250 is sewn to the top edge of front panel 226. Through the top opening defined by back panel 228 and elastic band 250 on front panel 226, the vinyl urine bag is inserted in pouch 220. As has been mentioned, a central opening in the bottom part of pouch 220 is provided for the projection therethrough of the drain valve in the vinyl urine bag. Additional reinforcing stitches 252 and 254 are used to sew together the front and back panels to render additional support for the urine bag as it is filled. As shown in FIG. 2, reinforcing stitches 252 and 254 comprise stitchings which are set apart from edge stitches 234 and 236 to define areas in which both front and back panels 226 and 228 are sewn together. The distance between reinforcing stitches and edge stitches is usually from about 10 to 15% of the length of back panel 228. For a pouch for carrying a conventional size urine bag, this distance is about 1 to 1½ inches.

The use of a two-way stretchable material as front panel 226 is of primary importance in the present invention. The stretchable front panel serves the following purposes:

(1) to allow the pouch to accommodate a larger volume of urine which can be collected in the urine bag.

(2) To hold the urine bag firmly within the pouch irrespective of the amount of urine contained therein. This is an extremely important function since without the stretchable front panel, the bag can shift as it is filled which will pull on the catheter connected thereto and cause pain in the patient. In addition, since the front panel is stretchable, uniform pressure is exerted on the front of the urine bag which prevents the urine bag from bulging at the bottom as it is filled. Hence, curling of the bottom portion of the bag towards the patient is eliminated.

(3) To offer the convenience of less frequent emptying of the bag due to increased usable volume therein.

To summarize, by using a stretchable front panel for the pouch, the urine bag is completely immobilized and bulging therein is eliminated. This leads to comfortable use of the urine collection system.

As shown in FIG. 2, front panel 226 has a length shorter than that of back panel 228 so as to provide easy access to buttons 244. However, front panel 226 should have such a length so that elastic band 250 does not restrict flow through the butterfly valve 708 (FIG. 7) provided in conventional vinyl urine bag 702. Preferably, front panel 226 has the length shown in FIG. 2, i.e. top elastic band 250 partially covers buttons 244. By using such a length, elastic band 250 presses against the inlet tube of the urine bag to immobilize and stabilize same. In addition, elastic band 250 allows easy and convenient visual inspection of the urine bag.

Upper and lower horizontal straps 242 and 244 are attached to back panel 228 for encircling the patient's leg so as to immobilize pouch 220. Upper strap 242 is attached to back panel 228 at two locations 252, 252 and at a distance equal to the width of back panel 228 so that stretching of the back panel is eliminated since strap 242 is made of a nonstretchable material. The first free end of strap 242 is fed through the loop portion 256 of a slip buckle. The hook portion 258 of the slip buckle may be provided on the second free end of strap 242. The following structural design is preferred since it is more comfortable to the patient. Hook portion 258 is attached to elastic band 260 which is folded over itself and interposed between back panel 228 and strap 242, the layers then secured by stitching 261 (see FIG. 5). A loop is preferred for the purposes of durability and strength. The length of folded elastic band 260 is shorter than the second free end of strap 242 so that strap 242 extends beyond hook portion 258. As a result, none of the metal portion of the slip buckle comes in contact with the patient's skin when strap 242 is encircled around the patient's leg. By using elastic band 260, the length defined by the looped strap can be varied so that the patient can change from a sitting to a standing position or vice versa without adjusting the length of the horizontal straps.

Similarly, lower horizontal strap 244 is attached to back panel 228 at locations 262 and 264 separated by the width of back panel 228 which prevents stretching of the back panel. The loop portion 266 of a slip buckle is provided on one free end of strap 244. The hook portion 268 of the buckle may be provided on the second free end of strap 244. It is preferred to use the structural hook design described above for the upper strap. That is to say, hook portion 268 is attached to elastic band 270 which is folded over and stitched between lower strap 244 and back panel 226. The second free end of strap 244 extends beyond elastic band 270 to prevent the slip buckle from coming into contact with the patient's skin when strap 244 is encircled around the patient's leg. The elastic band also permits stretching of the looped strap 244.

Both upper and lower horizontal straps are made of orthopedic woven belting. The upper strap has a width of 1½ inch and the lower strap, 1 inch. Both horizontal straps 242 and 246 serve to anchor and stabilize the pouch to the upper and lower thigh of the patient. The straps prevent the pouch from shifting due to weight increase resulting from the constantly increasing urine volume. The pouch is permitted to flex but not shift in response to continuous changes in trunk and leg position.

FIG. 3 shows the back view of the present urine leg drainage bag supporter. As can be readily seen, straps 242 and 244 extend beyond hook portions 258 and 268 of the slip buckles.

FIG. 4 shows the distribution of urine along the vertical axis of the urine bag as it is being filled. Due to the presence of stretchable front panel 226, the urine is prevented from collecting in the bottom portion of urine bag 802. In addition, drain valve 804 of urine bag 802 is prevented from curling toward the patient to cause discomfort. The stretchable front panel, reinforced stitches and anchoring lower strap 244 to back panel at 262 and 264 all contribute towards the elimination of curling.

FIG. 6 illustrates the construction of the lower end of the present carrier. As shown in FIG. 6, lower horizontal strap 244 is attached to back panel 228 at 262 and 264. Centrally disposed opening 240 is formed between front panel 226 and back panel 228.

As one skilled in the art would readily appreciate, the dimensions of the belt, straps and pouch can be varied in order to fit patients of various sizes and are not limited to those described above. The straps and belt are usually made of woven orthopedic belting. As can be readily seen, the materials used in forming the carrier should be easily cleaned or laundered and should not cause irritation to the patient's skin. Hence, the back panel is preferably made of woven terry cloth (nonstretch) or towel-like material so that irritation to the patient's skin from constant contact therewith is eliminated. The front panel is preferably formed of a knitted polyester material. As to fastener means, stainless steel slip buckles are preferred.

What is claimed is:

1. A pouch and support for a urine collection bag comprising:
   a waist encircling belt having adjustable length;
   a pouch for holding a urine bag, said pouch comprising front and back panel means, the vertical edges and part of the bottom edge of said front and back panel means being sewn together to define a top opening and a centrally disposed bottom opening, said front panel means being formed entirely of a stretchable material to hold a urine bag firmly within said pouch and further to prevent a urine bag from bulging at the bottom portion thereof as the bag is filled with urine;
   a plurality of vertical straps connecting said pouch to said belt, said vertical straps having variable lengths, and
   top and botton leg encircling straps extending from the top and bottom portions of said pouch, respectively, for encircling the leg of the wearer, said leg encircling straps having adjustable lengths and being provided with fastener means.

2. The supporter of claim 1 wherein each of said pouch encircling straps is attached to the back panel of said pouch at two locations, said locations being separated at a distance about equal to the width of said back panel.

3. The supporter of claim 2 wherein additional stitches are provided above the bottom edge stitches in said pouch to provide additional support for the urine bag.

4. The supporter of claim 1 wherein said fastener means comprises a slip buckle comprising hook and loop portions.

5. The supporter of claim 4 wherein each of the upper and lower leg encircling straps has first and second free ends, the first free end being fed through the loop portion of said slip buckle, the hook portion of said slip buckle being connected to an elastic band interposed between said back panel and said leg encircling strap, said elastic band having a length shorter than said second free end so that the second free end prevents said hook portion from contacting the wearer's skin.

6. The supporter of claim 1 wherein the upper edge of said front panel is provided with an elastic band.

7. The supporter of claim 6 wherein the front panel has a length shorter than that of the back panel.

8. The supporter of claim 1 wherein said pouch is provided with fastening means to which said urine bag can be attached.

9. The supporter of claim 1 wherein the belt and straps are made of a woven material; the back panel, terry cloth; the front panel, a knitted elastic material; and the fastener means, stainless steel.

* * * * *